United States Patent [19]

Soula et al.

[11] 3,965,158

[45] June 22, 1976

[54] PROCESS FOR PREPARING HALOPHENOL SULFONIC COMPOUNDS AND HALOPHENOLS FROM HALOBENZENE SULFONATES

[75] Inventors: Gerard Soula, Meyzieu; Jacques Metzger; Louis Lena, both of Marseille, all of France

[73] Assignee: Rhone-Progil, Courbevoie, France

[22] Filed: Dec. 27, 1973

[21] Appl. No.: 428,828

[30] Foreign Application Priority Data
Dec. 29, 1972 France .............................. 72.47213

[52] U.S. Cl. .......................... 260/512 R; 260/623 R
[51] Int. Cl.$^2$ ........................................ C07C 143/42
[58] Field of Search ..................... 260/512 R, 623 R

[56] References Cited
UNITED STATES PATENTS

| | | | |
|---|---|---|---|
| 2,835,707 | 5/1958 | Stosser et al. | 260/623 |
| 3,351,670 | 11/1967 | Belf | 260/623 R |
| 3,584,052 | 6/1971 | Gurien et al. | 260/512 R |
| 3,666,819 | 5/1972 | Michaels et al. | 260/623 R |
| 3,755,470 | 8/1973 | Michaels et al. | 260/623 R |

OTHER PUBLICATIONS
Schiessl et al., Chem. Abstract, 60, 1653 C (1964).

*Primary Examiner*—James O. Thomas, Jr.
*Assistant Examiner*—Nicky Chan
*Attorney, Agent, or Firm*—Bacon & Thomas

[57] ABSTRACT

Process for the selective ortho substitution of a halobenzene sulfonic acid compound with a hydroxyl group or a group convertible to same to prepare the corresponding halophenol sulfonic acid compound which process comprises reacting a halobenzene sulfonic acid compound having at least two halogen atoms at least one of which is ortho to the sulfonic group with an alkali metal hydroxide or other hydroxy containing compound which is capable of replacing a nuclear halogen atom with a hydroxyl group, said reaction being conducted in the presence of a liquid organic reaction medium which is responsible for the orientation of the hydroxyl substitution in the ortho position. The halophenol sulfonates thus prepared optionally may be desulfonated to obtain the ortho hydroxy halobenzene compound.

11 Claims, No Drawings

PROCESS FOR PREPARING HALOPHENOL SULFONIC COMPOUNDS AND HALOPHENOLS FROM HALOBENZENE SULFONATES

BACKGROUND OF THE INVENTION

The present invention relates to a process for preparing halophenol sulfonic compounds in which the hydroxyl group, or a derivative thereof, is in the ortho position with respect to the sulfonic group. More specifically, the present invention pertains to the alkaline hydrolysis of a polyhalobenzene-sulfonate in an organic solvent which solvent directly influences the ortho orientation of the nucleophilic aromatic substitution of the hydroxyl group for a halogen atom bound to the ring in the ortho position to the sulfonic group. The halophenol sulfonic acids obtained according to the present process may optionally be desulfonated to provide halophenol compounds which are difficult to obtain by heretofore known methods.

The displacement of a halogen atom from a polyhalobenzene sulfonate by reaction with a base to obtain halophenol sulfonates is known in the prior art. Exemplary of such processes are the reaction of sodium 2,4,5-trichlorobenzene sulfonate [Journal of the American Chemical Society, Vol. 74, pages 3890–91 (1958)], sodium 2,4-dichlorobenzene sulfonate (U.S. Pat. No. 2,835,707 granted May 20, 1958), or sodium 2,3,4-trichlorobenzene sulfonate (Czechoslovakia Pat. Nos. 105,281 and 105,282 filed Dec. 5, 1960) with a base to prepare the corresponding phenolic compounds. However, in these prior art processes, the reaction was conducted in an aqueous medium and the salts of para-hydroxy chlorobenzene sulfonic acids were the primary reaction products. Moreover, in order to effectuate the desired replacement reaction according to such processes, it was necessary to conduct the reactions under extreme temperature and pressure conditions.

SUMMARY OF THE INVENTION

It is therefore a primary object of the present invention to provide a facile process for the preparation of halophenol sulfonic acids from polyhalobenzene sulfonic acid compounds.

It is a further object of the invention to provide a process for producing halophenol sulfonic acids in which the hydroxyl group is ortho to the sulfonic acid group.

A further object is to provide a process for preparing halophenol sulfonic acids containing an ortho hydroxyl group which sulfonic acids may be desulfonated to afford the corresponding halophenol compounds.

Other objects, features and advantages of this invention will become more apparent to those skilled in the art from the detailed description of the invention which follows.

DETAILED DESCRIPTION OF THE INVENTION

The process of the instant invention is based upon the surprising discovery that the dielectric constant of an organic reaction medium influences the orientation of the hydroxy substitution reaction utilized in the preparation of halophenol sulfonic compounds from polyhalobenzene sulfonic acids. More particularly, it has been found that the halogen atom ortho to the sulfonic acid function in a polyhalobenzene sulfonic acid compound may be selectively displaced by a hydroxyl group or other alcohol containing group convertible to a hydroxyl function by effectuating the reaction in an organic medium having a room temperature dielectric constant not in excess of 25 and, further, that the substitution occurs almost exclusively in the ortho position if an organic reaction medium is selected which has a dielectric constant substantially less than 25 determined at room temperature.

The process according to the invention, therefore, comprises reacting a metallic salt of a polyhalobenzene sulfonic acid with a hydrolytic or saponification agent capable of replacing a halogen atom thereon with a hydroxyl group, or a derivative thereof, and conducting said reaction in an organic reaction medium having a particular dielectric constant, preferably less than or equal to 25 determined at room temperature.

The polyhalobenzene sulfonic acid starting material is utilized in the form of the metallic salt thereof and the preferred compounds are alkali metal halobenzene monosulfonates having two or more halogen atoms thereon, at least one of which is ortho to the sulfonate group. The halogens may be independently selected from the group consisting of chlorine, fluorine or bromine and accordingly the process is applicable to chlorobromobenzene sulfonic acid salts as well as polychloro-, polybromo-, or polyfluorobenzene sulfonates. Moreover, the benzene nucleus may optionally be substituted by an alkyl radical and lower alkyl substituted halobenzene sulfonates are especially preferred wherein the lower alkyl group is one having 1 to 5 carbon atoms. The foregoing starting materials are well known products simply obtainable by standard sulfonation reactions followed by salification. Illustrative polyhalobenzene sulfonate compounds suitable for use in the instant process include the salts of 2,4,5-trichlorobenzene sulfonic acid, 2,4-dichlorobenzene sulfonic acid, 2,3,4-trichloro benzene sulfonic acid, 2,3,4,5-tetrachlorobenzene sulfonic acid, 2,4-chlorobromobenzene sulfonic acid, 2,4-dichloro 5-bromobenzene sulfonic acid, 2,3-dichloro-4-methylbenzene sulfonic acid, 2,4-dichloro-5-ethylbenzene sulfonic acid, and the like.

The saponification, hydroxylation, or hydrolytic agents utilized in the practice of the present invention may be selected from alkali metal hydroxides, including lithium and sodium, or potassium alkali metal alcoholates or practically any other compound capable of effectuating the substitution of a halogen atom by a hydroxyl group or a derivative thereof, such as ethoxy, butoxy, propoxy, etc. which may later be converted to a hydroxyl group. The particular agent selected is not critical and, therefore, virtually any compound suitable for the hydroxylation of aryl halides may be utilized to accomplish the replacement reaction so long as the compound selected is capable of undergoing the desired reaction under the reaction conditions according to the instant process.

The presence of an organic solvent in the reaction mixture is a fundamental and critical feature of the process according to the invention and as outlined above, the organic solvent is determinative of the degree of ortho substitution obtainable according to the reaction method. In order to obtain the degree of ortho substitution necessary for commercial and economic feasibility an organic solvent is selected which has a dielectric constant not in excess of 25 at room temperature (20° – 25°C). Moreover, in order to most effectively utilize the discovered relationship between the dielectric constant of the reaction medium and the degree of ortho substitution and to facilitate the reaction process, it is advisable that the organic reaction medium function as a solvent for the various reactants and the organic solvent, therefore, is preferably one in which the reactants are entirely or at least substantially soluble at reaction temperatures. However, according to a specific embodiment of the process of the invention, a mixture of two or more solvents may be utilized only one of which functioning as a solvent for the reactants.

It is not necessary that the selected solvent be inert in the reaction, as long as the reaction product obtained in the reaction between the solvent and the halobenzene sulfonate salt can be easily converted to the desired phenolic compound. Thus, for example, the reaction may be carried out in an alcohol solvent which reacts with the halobenzene sulfonate to yield an ether which is easily converted into a phenol. In fact, the reaction may intentionally be conducted in the presence of a solvent which enters into the reaction such as, for example, where the desired product is a phenolic ether, i.e., 4,5-dichloro-2-butoxybenzene sulfonic acid. Without limiting the practice of the present invention to the hereinafter designated solvents, the instant process may be conducted in the presence of the following solvents which may be utilized alone or in combination: aliphatic alcohols, particularly those containing at least two carbon atoms in the chain, such as ethanol, butanols, isopropanol, pentanols, and hexanols; higher alcohols or oxo alcohols; cycloaliphatic alcohols such as cyclohexanol; benzylic alcohols; amines; and liquid polyethers having a terminal hydroxy group. Additionally, a variety of organic compounds having a minimal solvation action on the reactants may be utilized as cosolvents and these include, for instance, oxygenated heterocyclic compounds such as dioxan, tetrahydrofuran and the like.

The expression "substitution orienting liquid organic compound" is used herein to designate the aforementioned organic solvents and non solvating organic compounds utilized as the reaction medium according to the process of the invention which liquid organic compound preferentially directs the substitution of a halogen atom ortho to the sulfonic group in the polyhalobenzene sulfonate starting material by a hydroxyl group or other substituent which may then be converted to a hydroxyl group.

The molar ratio between the saponification agent and the halobenzene sulfonate salt is not critical and, therefore, may vary between 1/1 and 20/1, but is preferably between 3/1 and 10/1.

However, it has been determined that the initial concentration of the hydroxylation agent in the mixture may effect the selectivity of the substitution in the ortho position and, therefore, depending upon the dielectric constant of the solvent utilized there exists a certain minimal saponification agent concentration which must be maintained in order to accomplish the desired substitution reaction. More specifically, it has been observed that irrespective of the organic solvent utilized, the quantity of alkaline reactant influences the degree of ortho orientation; however, the effect is most significant when the reaction is conducted in a solvent having a dielectric constant at room temperature which approaches the maximum stated value of 25. As previously noted, solvents having a relatively low dielectric constant are responsible for a high rate of substitution in the ortho position and, therefore, the utilization of increased amounts of alkaline reactant will have little or no effect on the degree of ortho substitution. Contrariwise solvents having a higher dielectric constant exert a less marked effect on the level of ortho substitution and consequently, the concentration of the saponification agent may have a significant effect on the degree of ortho substitution and may be utilized to augment the ortho orientation properties of an organic reaction medium having higher dielectric constants.

The foregoing interplay between the concentration of the saponification agent and the organic solvent with respect to the relative orientation properties of each may be advantageously utilized to afford enhanced flexibility to the process according to the invention inasmuch as the rate of ortho selectivity in the preparation of ortho halophenol sulfonic compounds can be adjusted by varying the quantity of the saponification agent in the mixture dependent upon the solvent selected. Consequently, the minimum quantity of saponifying reactant which can be utilized in the reaction may vary over a wide range depending upon the chosen solvent and the desired rate of ortho selectivity and the concentration of the saponification agent is most advantageously determined by preliminary testing. Generally, however, it may be stated that a high proportion of ortho hydroxyhalobenzene sulfonic compounds is readily obtainable utilizing 0.5 to 0.8 moles of saponification agent per liter of solvent when an organic solvent having a low dielectric constant is selected. Of course, when the reaction is carried in a solvent having a relatively high dielectric constant, the initial concentration of the saponification agent is much more significant and the concentration of same may desirably be increased. Under the foregoing conditions, therefore, there is no absolute upper limit for the concentration of the saponification or hydrolytic agent other than inherent technological or economic considerations, and solely from the standpoint of these economical and technological limitations on the maximum utilizable concentrations, it is generally deemed advisable to restrict the maximum quantity of the hydroxylation reactant to approximately 4 moles per liter of liquid organic reaction medium.

The concentration of the metallic salts of the halobenzene sulfonic compound is not critical and the concentration may, therefore, range between 0.5 moles and 1 mole, preferably between 0.1 and 0.5 moles of sulfonate reactant per liter of solvent.

The reaction process is advantageously carried out by maintaining the reaction mixture at a temperature generally between 100° and 250°C. and preferably between 140°C. and 170°C. and allowing the reaction to continue for a time sufficient to allow the halogenated benzene sulfonate starting material to be substantially converted to the desired product. In the event that the boiling point of the organic reaction medium utilized in the reaction mixture is lower than the desired reaction temperature, the process may be carried out under pressure to maintain the reaction mixture in the liquid phase.

Upon completion of the reaction, the reaction mixture contains halophenol sulfonates, primarily in the form of salts derived from the metal contributed by the saponification agent, and optionally phenolic derivatives of the solvent if the solvent utilized is reactive. The constituents of the reaction mixture may be isolated by any well known method, including for example evaporation of the solvent and dilution of the residue with water followed by precipitation of the phenolic compounds by acid hydrolysis. Moreover, it is possible according to the process of the invention to merely remove the solvent, dilute the solid residue with water and neutralize the resultant mixture and then directly convert the resultant aqueous solution by desulfonation to obtain halophenols.

The process according to the invention may be advantageously utilized to provide a direct synthetic process for producing halophenols, for example, 3,4-dichlorophenol, 2,3,4-trichlorophenol and 2,3,4,5-tetrachlorophenol all of which are difficult to obtain in the pure state by the heretofore utilized processes of chlorination of phenols or the direct saponification of chlorobenzenes. An attendant advantage of the instant process is the avoidance of the formation of noxious by-products such as halodibenzodioxanes, which typically appear during the direct saponification of halobenzenes.

Where it is desired to desulfonate the halophenol sulfonic compounds obtained according to the process of the instant invention, such desulfonation and optionally hydrolysis of the resultant compounds may be accomplished according to conventional methods, such as by heating the aqueous solution obtained by the method outlined above with a strong mineral acid such as hydrochloric acid, sulfuric acid or phosphoric acid.

It is, of course, evident that the halophenol sulfonic compound may be isolated prior to converting same into the halophenols.

In order to further illustrate the present invention and the advantages thereof, the following specific examples are given, it being understood that the same are intended only as illustrative and in no wise limitative.

EXAMPLE 1

0.2 moles of sodium 2,4,5-trichlorobenzene sulfonate, 0.06 moles of sodium hydroxide (pellets) and 50 ml. of 2-butanol (dielectric constant of 15.8 at 25°C.) were introduced into a reaction vessel. The mixture was heated at 165°C. for two hours. After cooling, the alcohol was evaporated and the residue diluted with 100 ml. of water and neutralized with phosphoric acid. The aqueous solution thus obtained contained sodium 4,5-dichloro 2-hydroxy benzene sulfonate and sodium 4,5-dichloro 2-butoxy benzene sulfonate. The rate of conversion of the sulfonate starting material to the phenolic and butoxy derivatives was determined by titration of the chloride ions formed during the reaction and was found to be 100%. The selectivity of the substitution of the chlorine in the ortho position to the sulfonate was determined by vapor phase chromatographic analysis of the chloro phenols obtained from the above-mentioned aqueous solution.

In order to convert the 2-butoxy compound obtained above into the corresponding dichlorophenol, 100 ml. of phosphoric acid was poured into a flask fitted with an agitator, dropping funnel and distillation apparatus and the reaction medium was heated at 160°C. Then the aqueous solution containing the 2-butoxy and 2-hydroxybenzene sulfonates was gradually added while keeping the temperature at 160°C. to 170°C. The chlorophenol product distilled off in the form of an azeotrope of water and chlorophenol. Near the end of the distillation process, which proceeded for approximately 1½ hours, a small quantity of water was added to enhance the recovery of the phenol.

The proportion of 3,4-dichlorophenol in relation to the total yield of all chlorophenol isomers (which indicates the selectivity of the substitution of the ortho chlorine atom) in the distillate was found to be 93%.

EXAMPLES 2 – 9

The process of Example 1 was repeated starting with various reactant materials and utilizing various liquid organic compounds as the reaction medium. The ratio of sulfonate reactant to solvent was the same as in Example 1, but the concentration of the saponification agent and the temperature of the reaction were varied.

The reaction conditions, specific reactants and the results obtained therewith are set forth in Table 1 hereinbelow.

TABLE 1

| Example Number | Halobenzene sulfonate | Solvent | Saponifying agent | Concentration of saponifying agent in moles/liter of solvent | Temperature (°C.) | Selectivity of the substitution in the ortho position |
|---|---|---|---|---|---|---|
| 2 | sodium 2,4,5-trichlorobenzene sulfonate | cyclohexanol (a) | sodium hydroxide | 0.6 | 145°C | 96% |
| 3 | sodium 2,4,5-trichlorobenzene sulfonate | tert-butanol | sodium hydroxide | 0.6 | 180°C | 95% |
| 4 | sodium 2,4,5-trichlorobenzene sulfonate | 1-butanol | sodium butanolate | 0.6 | 105°C | 93% |
| 5 | lithium 2,4,5-trichlorobenzene sulfonate | 2-butanol | lithium butanolate | 0.6 | 170°C | 96% |
| 6 | sodium 2,4,5-trichlorobenzene sulfonate | 2-butanol (80% vol.) dioxan (20% vol.) | sodium hydroxide | 0.5 | 170°C | 96% |
| 7 | sodium 2,3,4,5-tetrachlorobenzene sulfonate | 2-butanol (80% vol.) dioxan (20% vol.) | sodium hydroxide | 0.5 | 165°C | 96% |
| 8 | sodium 2,3,4,5-tetrachlorobenzene sulfonate | cyclohexanol (a) | sodium hydroxide | 0.6 | 130°C | 95% |
| 9 | sodium pentachlorobenzene sulfonate | 2-butanol | sodium hydroxide | 0.6 | 160°C | 91% |

(a) test carried out at atmospheric pressure.

In each of the foregoing examples, the conversion rate was determined by titration of the chloride ions and was found to be 100%. The selectivity of the ortho substitution was determined as set forth in Example 1.

EXAMPLE 10

.01 moles of sodium 2,4,5-trichlorobenzene sulfonate and .03 moles of sodium hydroxide in 50 mls. of isopropanol (dielectric constant of 18 at 25°C.) were heated at 160°C. for 2 hours. The selectivity of the substitution of the ortho chlorine atom was 78%.

The same reaction was repeated utilizing .2 moles of sodium hydroxide instead of .03 moles and the selectivity of ortho substitution was increased to 90% which shows the effect the concentration of the saponification agent has on the ortho orientation in an otherwise identical reaction mixture.

EXAMPLE 11

.01 moles of sodium 2,3,4,5-tetrachlorobenzene sulfonate and .03 moles of sodium hydroxide in 50 mls. of 2-butanol were heated for 2 hours at 150°C. The selectivity of chlorine substitution in the ortho position was determined to be 88%.

The foregoing reaction process was repeated except that the concentration of the sulfonate reactant was increased to .02 moles and the sodium hydroxide concentration was increased to .06 moles. The rate of ortho substitution was found to be increased to 92%.

EXAMPLE 12

.01 moles of sodium 2,4,-dichloro 5-bromo benzene sulfonate and .03 moles of sodium hydroxide in 50 mls. of cyclohexanol (dielectric constant of 15° at 25°C.) were heated for 1 hour at 140°C. under atmospheric pressure with constant stirring. After cooling, the cyclohexanol was removed by steam distillation and the residue was neutralized with aqueous hydrochloric acid. Desulfonation was carried out according to the procedure set forth in Example 1. The halophenols obtained contained 75% by weight of 3-chloro 4-bromo phenol.

Thus, there is provided by the present invention a process for selectively substituting a halogen atom in the ortho position in a halobenzene sulfonate with a hydroxyl group or a group easily converted to a hydroxyl group by merely conducting the reaction in a particular organic reaction medium thereby resulting in the preparation of ortho hydroxy halobenzene sulfonates which may be easily desulfonated to yield halophenols.

While the invention has been described and pointed out with reference to certain preferred embodiments thereof, those skilled in the art will appreciate that various changes and modifications and substitutions can be made without departing from the spirit of the invention. It is intended therefore, that the invention be limited only by the scope of the claims which follow.

What is claimed is:

1. In a process for the preparation of a halophenol sulfonic acid compound or phenolic ether thereof or a lower alkyl substituted derivative of said halophenol sulfonic acid compound or phenolic ether derivative in which the phenolic hydroxy or ether group thereof is in the ortho position, comprising the reaction of a metal salt of a polyhalobenzene monosulfonic acid or lower alkyl substituted derivative thereof with a hydroxylating agent selected from the group consisting of alkali metal hydroxides and alkali metal lower alkoxides, the improvement comprising conducting said reaction in the presence of at least one ortho substitution orienting liquid organic compound having a dielectric constant not in excess of 25 determined at approximately 25°C. functioning as a reaction medium and selected from the group consisting of alkanols, cycloalkanols, oxoalcohols, benzylalcohols, amines, liquid poly ethers having a terminal hydroxy group thereon and mixtures thereof at a temperature between about 100°C. and 250°C., maintaining the molar ratio of said hydroxylating agent and said polyhalobenzene sulfonate salt between about 1/1 and 20/1, with the proviso that when said ortho substitution orienting liquid organic compound has a dielectric constant approximately equivalent to 25 at 25°C. the concentration of said hydroxylating agent is increased to compensate for the decreased selectivity of said ortho substitution orienting liquid organic compound, and recovering the halogenated phenolic compound.

2. The process as defined by claim 1, wherein said substitution orienting organic compound has a dielectric constant less than 25 determined at 25°C.

3. The process as defined by claim 1, wherein said substitution orienting liquid organic compound is a solvent for the reactants present in the reaction mixture.

4. The process as defined in claim 1, wherein said substitution orienting liquid organic compound is an alkanol or cycloalkanol.

5. The process as defined by claim 1, wherein said liquid organic compound is butanol.

6. The process as defined by claim 1, wherein said liquid organic compound is cyclohexanol.

7. The process as defined by claim 1, wherein said liquid organic compound is an oxo alcohol.

8. The process as defined by claim 1, wherein said liquid organic compound is a liquid polyether having a terminal hydroxyl group thereon.

9. The process as defined by claim 1, wherein the molar ratio of the hydroxylating agent and the polyhalobenzene sulfonate salt is between 3/1 and 10/1.

10. The process as defined in claim 1, wherein said substitution orienting liquid organic compound is benzyl alcohol.

11. The process as defined by claim 1, wherein a cosolvent selected from the group consisting of dioxan and tetrahydrofuran is employed in combination with said at least one ortho substitution orienting liquid organic compound.

* * * * *